United States Patent [19]
Nakamura

[11] Patent Number: 5,295,989
[45] Date of Patent: Mar. 22, 1994

[54] LIGHT CABLE FOR USE IN AN APPARATUS FOR OPHTHALMIC OPERATION USING A LASER BEAM

[75] Inventor: Hirokazu Nakamura, Aichi, Japan
[73] Assignee: Nidek Co., Ltd., Gamagori, Japan
[21] Appl. No.: 889,995
[22] Filed: May 29, 1992
[30] Foreign Application Priority Data
May 31, 1991 [JP] Japan ................... 3-157867
[51] Int. Cl.$^5$ .............................. A61B 17/32
[52] U.S. Cl. ........................... 606/4; 606/10; 606/16
[58] Field of Search ............... 606/10, 11, 15, 16, 606/17, 19

[56] References Cited
U.S. PATENT DOCUMENTS
3,910,276 10/1975 Polanyi et al. ........................ 606/10
4,686,979 8/1987 Gruen et al. .......................... 606/15
5,226,903 7/1993 Mizuno ................................. 606/4

*Primary Examiner*—Stephen C. Pellegrino
*Assistant Examiner*—Sonya C. Harris
*Attorney, Agent, or Firm*—Finnegan, Henderson, Farabow, Garrett & Dunner

[57] ABSTRACT

A light cable in an apparatus for ophthalmic operation using a laser beam, which introduces the laser beam into a delivery optical system by being connected with the apparatus body in which a laser system and a laser control system are provided, is disclosed. The light cable is constituted of a number of optical fibers for illumination light and a optical fiber for laser beam constitute, which optical fibers for illumination light are arranged around the optical fiber for laser beam in at least the end of emitting light beam of the optical fibers.

2 Claims, 2 Drawing Sheets

LIGHT CABLE FOR USE IN AN APPARATUS FOR OPHTHALMIC OPERATION USING A LASER BEAM

BACKGROUND OF THE INVENTION

1. Field of the Invention

The present invention relates to a light cable, and more particularly to a light cable for use in an apparatus for ophthalmic operation using photocoagulation by a laser beam.

2. Description of Related Art

Conventionally, there is an apparatus for ophthalmic operation using photocoagulation, which photocoagulates an affected part of a fundus of a patient's eye by applying a laser beam.

During the ophthalmic operation by photocoagulation using said apparatus as mentioned above, the ophthalmologist observes the patient's eye through the observing optical system, like an ophthalmic operation microscope, so that it is necessary to introduce the laser beam into the optical path of the observing system in the microscope.

Usually, an optical fiber is used to transfer the laser beam from the apparatus body which includes a laser system and its control system to a laser delivering system which includes optics which defines the irradiation area. The laser delivering system is attached to the observing system of the microscope to be optically coaxialized.

In one conventional method, the illumination system of the ophthalmic operation microscope is utilized. The optical axis of laser beam becomes coaxial with that of the observing system by means of installing a mirror which is positioned to reflect the laser beam to be coaxial with the optical axis of the observing system. However, in order that the optical axis of the illuminating system be inclined with about 4 degrees to the optical axis of the optical system for irradiating the laser beam, the illuminated visual field sometimes does not correspond with the range of movement of the laser beam, so that the laser beam irradiates out of the illuminated visual field.

In a second conventional method, the optical axis of the optical system for irradiating the laser beam is coaxial with the optical axis of the optical system for illumination, that is, the center of the optical system is occupied by the laser transmitting system and the circumference thereof, without interfering with the laser transmitting system, is occupied by the illuminating system.

However, when using the second method, it is necessary that a small mirror be arranged in the optical system, to adjust the two optical systems so as to be coaxial without interfering mutually. Thus, the optical system is complicated in this combination so that the adjustment of the optical system becomes difficult. Because of the apparatus becoming large in size, it is difficult to be installed in a simple type microscope.

Further, according to the second method mentioned above, the optical axis of the laser irradiating optical system and the optical axis of the illumination optical system are coaxial, but each beam is transmitted through separate space, and, depending on circumstances, only the illumination light is shut off before reaching the fundus of the patient's eye. As a result, a problem like that in the first method occurs.

SUMMARY OF THE INVENTION

The present invention has been made in view of the above circumstances and has an object to overcome the above problems and to provide a light cable in an apparatus for ophthalmic operation, wherein the optical axis of the optical system for irradiating the laser beam becomes coaxial with the optical axis of the optical system for illumination by using a simple mechanism.

Further, another object of the present invention is providing a light cable in a separatus for ophthalmic operation, which can be easily installed in a simple type ophthalmic operation microscope.

Additional objects and advantages of the invention will be set forth in part in the description which follows and in part will be obvious from the description, or may be learned by practice of the invention may be realized and attained by means of the instrumentalities and combinations particularly pointed out in the appended claims.

To achieve the objects and in accordance with the purpose of the invention, as embodied and broadly described herein, the light cable in an apparatus for ophthalmic operation using a laser beam of this invention, which introduces the laser beam into a delivery optical system by being connected with the apparatus body in which a laser system and a laser control system are included, comprises a number of optical fibers for illumination light on which the illumination light is incident, and an optical fiber for a laser beam on which the laser beam is incident, wherein the optical fibers for illumination light are arranged around the optical fiber for laser beam at least at the emitting light beam of the optical fibers.

In the light cable, the optical fiber for laser beam is arranged almost in the center of the optical fibers for illumination light, and the delivery optical system is mounted in an ophthalmic operation microscope.

Further, in the light cable, the delivery optical system is mounted in an ophthalmic operation microscope, and the optical fibers for illumination light are connected with an illumination unit fixed in a pole which supports the ophthalmic operation microscope.

The apparatus body for ophthalmic operation using the laser beam, with which the optical fiber is connected, comprises a relay box into which the laser beam is introduced and the control signal for the apparatus can be input, the optical fiber for laser beam is connected with the relay box.

According to the light cable of the present invention, the optical axis of the optical system for irradiating the laser beam and the axis of the optical system for illumination are made coaxial by simple mechanism, and further, the light cable can be easily installed in a simple type ophthalmic operation microscope.

BRIEF DESCRIPTION OF THE DRAWINGS

The accompanying drawings which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of a light cable in an apparatus for ophthalmic operation using photocoagulation embodying the present invention will now be given referring to the accompanying drawings.

Figure 1:
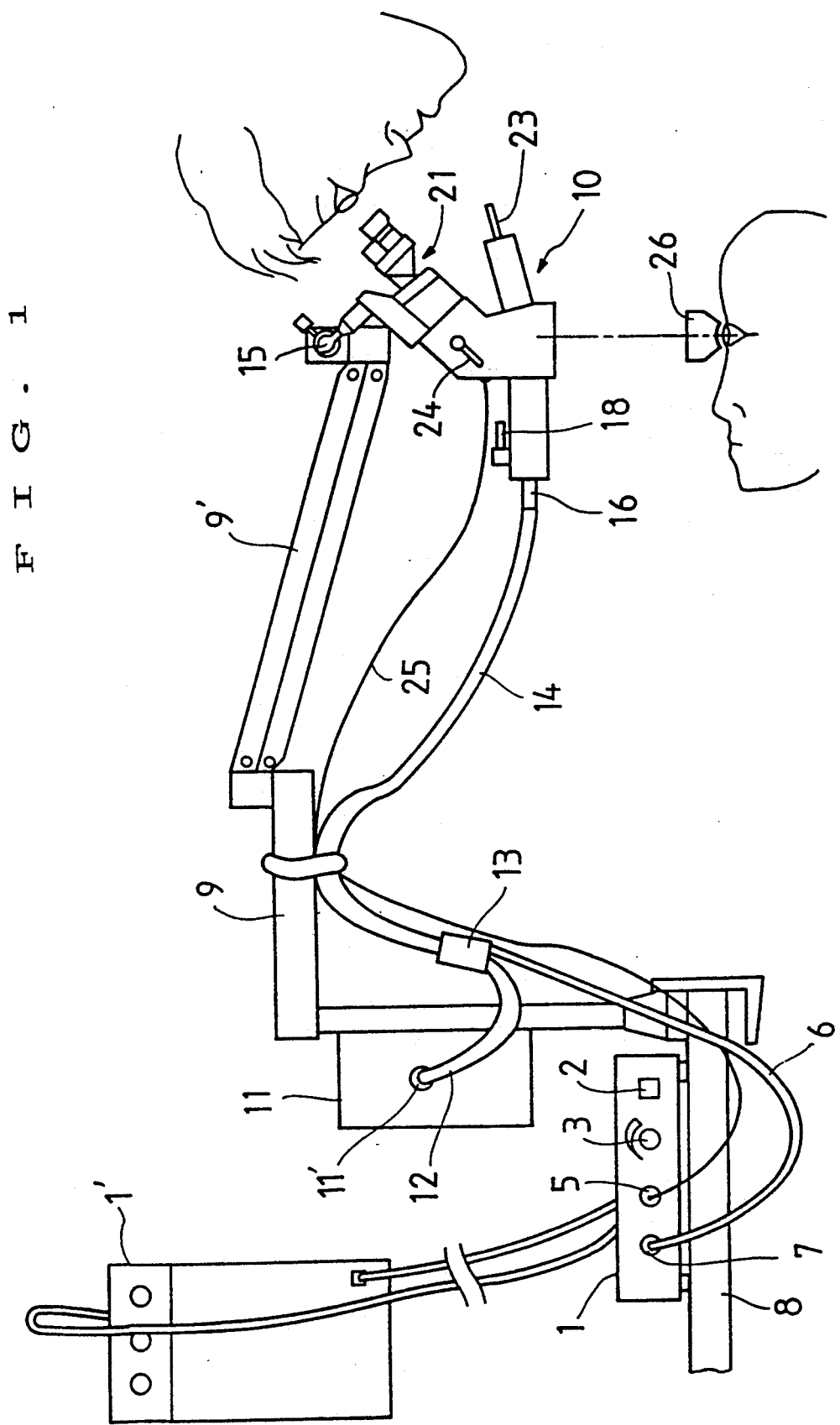
FIG. 1 is a schematic view of the apparatus for ophthalmic operation using photocoagulation embodying this invention.

In FIG. 1, there is shown an apparatus for ophthalmic operation using photocoagulation by argon laser beam comprising a light cable of this invention. A relay box 1 with which an apparatus body 1' is connected through cables and an arm 9, which includes a connecting member 9', are arranged on a table 8. The relay box 1 is provided with a main switch 2, a knob 3 for adjusting the aiming light, a connector 5 to receive the signal of a filter 4 for protecting the oculist's eye, and a connector 7 into which a photocoagulation can be introduced.

At the end of the connecting member 9' of the arm 9, an operation adaptor 10 with an operation microscope operates as a delivery unit of the apparatus, and is supported through a ball joint 15 so that the adaptor 10 is movable and rotatable.

A light source box 11 is fixed on the arm to provide illumination. The box 11 comprises a halogen lamp in the interior thereof and a connector 11' into which an illumination cable 12 can be inserted.

The cable 6 for transmitting the laser beam for photocoagulation is composed of a light fiber made from quartz covered by a resin film. In this embodiment, the light fiber has a diameter of about 250 μm.

The cable for illumination 12 is composed of a number of light fibers made from quartz covered by the resin film wherein the one light fiber has a diameter of about 50 μm. Further, the fiber is preferably as fine as possible within a practicable diameter.

Figure 4:
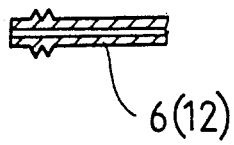
FIG. 4 is a sectional view of the end of the light cable.

The cable for illumination cable 12 and the photocoagulation cable 6 have an end in the form of plug shown in FIG. 4 so as to be able to be inserted in the connector 7, 11 respectively.

Figure 2:
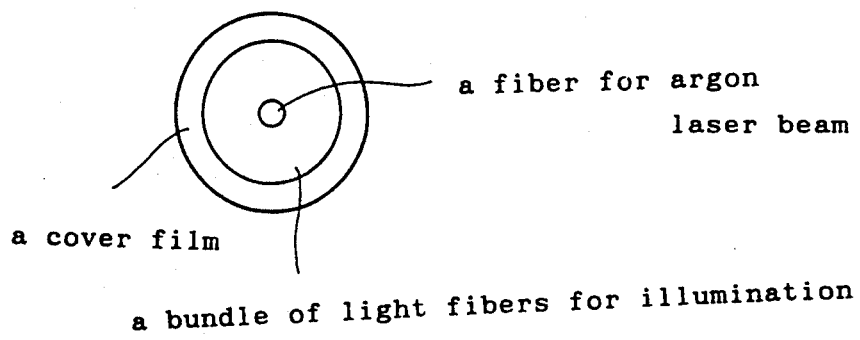
FIG. 2 is a sectional view of the light cable.

As shown in FIG. 2, the light fiber of the photocoagulation cable 6 and the light fibers of the illumination cable 12 are bundled together so that the light fiber for photocoagulation is in the center. Further, the light fibers are formed into a bundled cable 14 so that the fiber portion thereof has a predetermined diameter preferably of about 4 mm.

As mentioned above, the photocoagulation light fiber is at the center of the light cable 14, it is easy to design the optical system of adaptor including a diaphragm to enable the fundus of the patient's eye to be observed by positioning the aiming light in a center of the illumination light spot.

Figure 3:
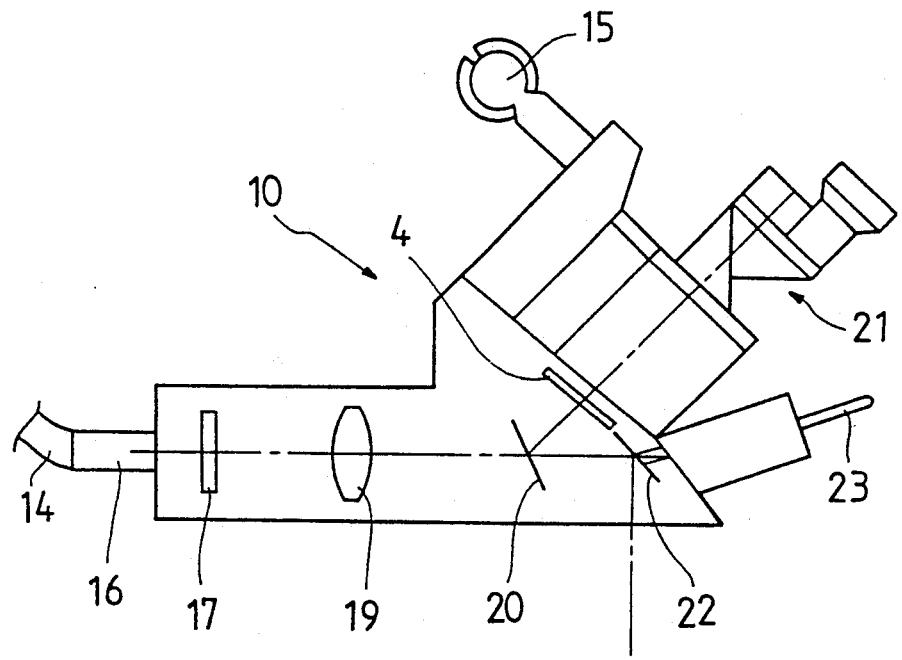
FIG. 3 is a schematic partial view of the optical system of the adaptor with a opthalmic operation microscope.

In FIG. 3, there is shown the optical system of the adaptor portion in the ophthalmic operation microscope 10 which is the delivery unit of the apparatus.

In one end of the adaptor 10, a connector 16 is disposed to connect with the emitting end of the light cable 14. The adaptor 10 comprises a diaphragm 17 for illumination which is movable into and out of the optical path of the optical system by a lever 18, (FIG. 1) lens 19 which is selected so as to conjugate the emitting end of the cable 14 with the fundus of the patient's eye. Additionally, in this embodiment, the lens 19 has a 2.5 magnification so that the spot of the illumination light on the fundus of the patient's eye has a diameter of about 10 mm.

Further, the adaptor 10 comprises a couple of mirrors 20, 20 which are arranged separately on the right and the left of the optical path of photocoagulation light so as not to obstruct the optical path, and a mirror 22 which is arranged so as to be movable at any angle by a manupulator 23. Therefore, the mirror 22 irradiates the light beam transmitted from the cable 14 into the fundus of the patient's eye to be treated and reflects the light from the patient's eye to the mirrors 20, 20, so that the mirrors 20, 20 send the light from the patient's eye into a microscope 21.

The protecting filter 4 mentioned above is arranged in the adaptor 10 so as to be movable into and out of the observation optical path by a lever 24 (FIG. 1), and with which a sensor (not shown) is connected. Based on a sensor signal transmitted to the relay box through the cable 25, a safety mechanism of the apparatus body 1' operates so as to move the protecting filter 4 into the optical path and thereby enable irradiation of a photocoagulation laser beam. The oculist's eye is accordingly protected. Any suitable sensor may be employed to sense the position of the lever 24.

During the ophthalmic operation, a contact lens 26 is arranged in the patient's eye. According to the above apparatus, the operation occurs as follows.

First, when a key photocoagulation switch of the apparatus body 1' and a main switch 2 of the relay box 1 are turned on, the laser beam can be out put at the push of a foot switch (not shown). Only the aiming light is emitted for a while after turning on the main switch 2, which is introduced into the optical system in the adaptor portion of the adaptor with a microscope 10 through the photocoagulation cable 6 and the cable 14.

Next, the illumination light is emitted when the switch is turned on for the illumination light source 11, and further is transmitted to the optical system of the adaptor through the illumination cable 12 and the cable 14. Therefore, the fundus of the patient's eye is irradiated by the illumination light through the optical system of the adaptor with the aiming light.

When the affected part of the patient's eye to be photocoagulated is found, while the patient's eye is illuminated by light, the aiming light is focused on the affected part of the patient's eye, which is in the center of the spot of the illumination light in order that the photocoagulation fiber is disposed in the center of the fiber bundle.

Next, after being aimed, the affected part is photocoagulated by the argon laser beam at a push of the foot switch, which argon laser beam is irradiated to the affected part of the patient's eye through the same path as the path of the aiming light. During photocoagulation, the oculist's eye is protected with the protecting filter 4.

The present invention may be embodied in other specific forms without departing from the spirit or essential characteristics thereof. For instance, in the above embodiment, although the binder 13 is arranged in the middle of the cable, the same result can be obtained by forming a bundle in at least one emitting end.

Furthermore, the light cable of the present invention can be used not only with the ophthalmic operation microscope as mentioned above, but with an adaptor in a slit-lamp.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic operation apparatus using a laser beam, in which the laser beam is introduced to a patient's eye for ophthalmic operation, the apparatus comprising:
   a body in which a laser beam oscillator is disposed;
   a source of illumination light;
   an ophthalmic operation microscope for observing an affected part of the patient's eye;
   a delivery optical system, mounted in said ophthalmic operation microscope, for introducing the laser beam and the illumination light into the patient's eye;
   a light cable connecting the apparatus with the delivery optical system, including a plurality of optical illumination fibers on which the illumination light is incident and an optical laser fiber on which the laser beam is incident, wherein said optical illumination fibers are arranged around the optical laser fiber at least at an end of the cable where an illumination light beam of the optical illumination fibers is emitted, and the end of the cable is arranged at a conjugate position with the affected part of the eye to the delivery optical system.

2. An ophthalmic operation apparatus using a laser beam according to claim 1 wherein the opthalmic operation microscope further comprises a pole for supporting the ophthalmic operation microscope, and the source of illumination light includes an illumination unit fixed in said pole and having the optical illumination fibers connected thereto.

* * * * *

UNITED STATES PATENT AND TRADEMARK OFFICE
CERTIFICATE OF CORRECTION

PATENT NO. : 5,295,989
DATED : March 22, 1994
INVENTOR(S) : Hirokazu Nakamura

It is certified that error appears in the above-indentified patent and that said Letters Patent is hereby corrected as shown below:

Claim 1, column 6, line 5, after "connecting" insert the following authorized Examiner's Amendment: --the illumination light source and the laser beam oscillator (of)--.

Signed and Sealed this

First Day of November, 1994

BRUCE LEHMAN

Attest:

Attesting Officer

Commissioner of Patents and Trademarks